United States Patent [19]
Simonian et al.

[11] Patent Number: 6,099,568
[45] Date of Patent: Aug. 8, 2000

[54] ACL GRAFT FIXATION DEVICE AND METHOD

[75] Inventors: Peter T. Simonian, Seattle, Wash.; Bartolome J. Salazar, Clearwater, Fla.

[73] Assignee: Linvatec Corporation, Largo, Fla.

[21] Appl. No.: 09/033,245

[22] Filed: Mar. 3, 1998

[51] Int. Cl.⁷ ..................................................... A61F 2/58
[52] U.S. Cl. ....................................................... 623/13.11
[58] Field of Search ......................................... 623/13, 16

[56] References Cited

U.S. PATENT DOCUMENTS

| | | | |
|---|---|---|---|
| 3,896,500 | 7/1975 | Rambert et al. ................................. | 3/1 |
| 4,708,132 | 11/1987 | Silvestrini . | |
| 4,744,793 | 5/1988 | Parr et al. . | |
| 4,997,433 | 3/1991 | Goble et al. . | |
| 5,139,520 | 8/1992 | Rosenberg . | |
| 5,152,790 | 10/1992 | Rosenberg et al. . | |
| 5,156,616 | 10/1992 | Meadows et al. . | |
| 5,261,914 | 11/1993 | Warren . | |
| 5,306,290 | 4/1994 | Martins et al. . | |
| 5,306,301 | 4/1994 | Graf et al. . | |
| 5,380,334 | 1/1995 | Torrie et al. . | |
| 5,464,424 | 11/1995 | O'Donnell, Jr. ......................... | 606/228 |
| 5,522,843 | 6/1996 | Zang . | |
| 5,584,835 | 12/1996 | Greenfield . | |

FOREIGN PATENT DOCUMENTS

1916122C1  8/1997  Germany .

OTHER PUBLICATIONS

"The Paramax ACL Guide System Surgical Technique," brochure, Linvatec Corporation, 1992.

*Primary Examiner*—Mickey Yu
*Assistant Examiner*—Alvin Stewart
*Attorney, Agent, or Firm*—Michael de Angeli

[57] ABSTRACT

An improved anchor for securing a graft ligament in place in a bone tunnel comprises a dome portion surrounded by a flange portion. The dome portion fits into a bone tunnel and includes first and second apertures for receiving sutures located on so that the anchor is positioned stably in use, while the flange portion abuts the outer surface of the bone and supports the anchor. The cross-sectional thickness of the anchor is increased in the area of the apertures to provide adequate pull-out strength. The flange may be elliptical in plan and the dome portion asymmetric, to allow the anchor to better withstand tension.

8 Claims, 2 Drawing Sheets

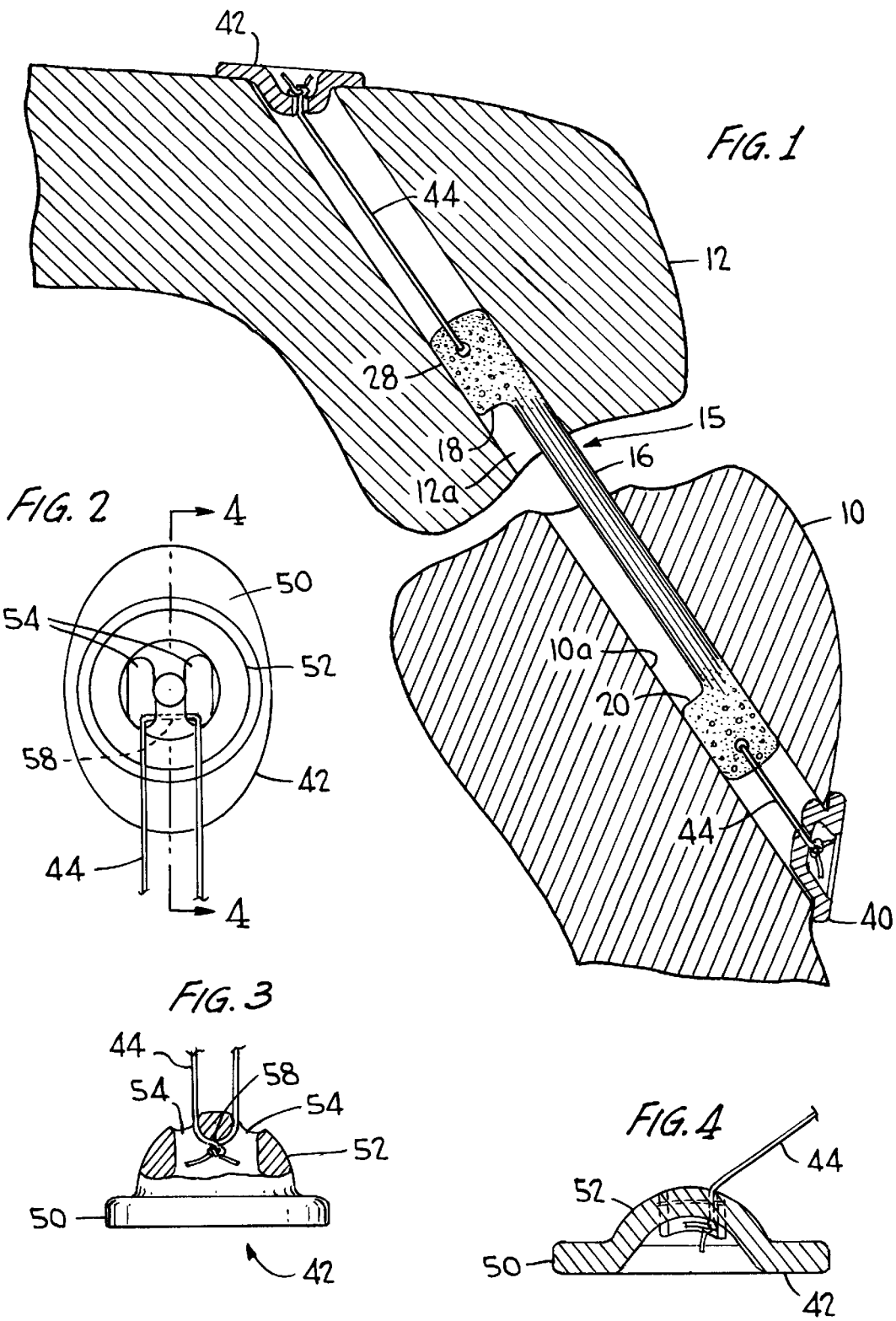

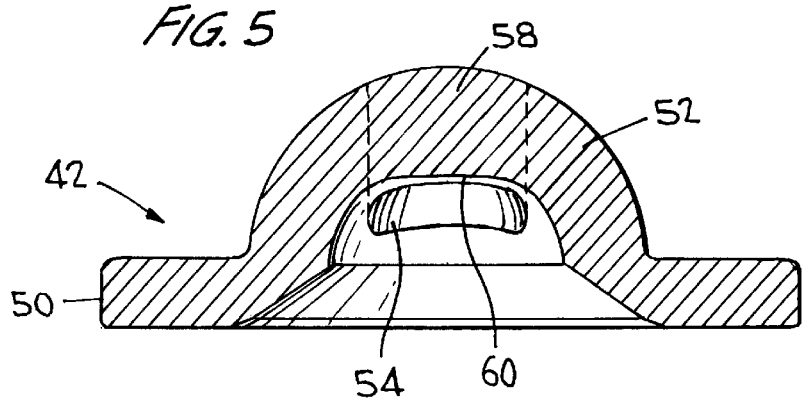
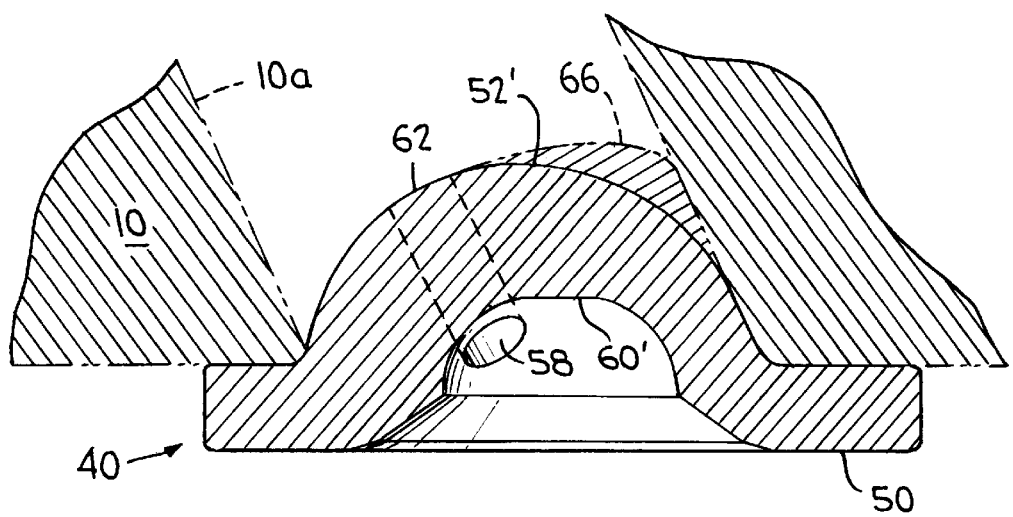

ACL GRAFT FIXATION DEVICE AND METHOD

FIELD OF THE INVENTION

This application relates to devices for simplifying and rendering more reliable the attachment of graft ligaments to bone, for example, for replacement of ligaments such as the anterior cruciate ligament and similar structures.

BACKGROUND OF THE INVENTION

Due to the frequency of injury to the anterior cruciate ligament (ACL), especially in sports, and similar injury to other ligaments and related structures, there is a great deal of prior art dealing with replacement of these structures with graft ligaments. Much of this prior art is concerned principally with ensuring proper alignment of bone tunnels drilled in the tibia and femur to receive the opposed ends of the graft ligament, with proper preparation of the surgical site, i.e., by removing sufficient bone to allow the graft to function properly, and with preparation of suitable graft ligaments, commonly by harvesting donor bone/tendon/bone structures from the knee of the patient. See generally, "The Paramax ACL Guide System Surgical Technique", a brochure published by Linvatec Corporation of Largo, Florida in 1992, and incorporated by reference herein, which provides useful background on one type of overall ACL replacement procedure. Other sources of replacement ligaments, including allograft and autograft ligament substitutes, are within the skill of the art and are intended to be included within "graft ligament" as used herein.

The present invention does not address these aspects of ACL reconstruction, but instead addresses the problem of securely anchoring the graft ligament in the bone tunnels. More specifically, the present invention relates to improvements in devices to be disposed at the outer ends of bone tunnels to provide a fixing point for sutures securing an end of a graft ligament in place.

The prior art shows numerous devices for anchoring sutures for holding graft ligaments in place. For example, Zang U.S. Pat. No. 5,522,843 and Greenfield U.S. Pat. No. 5,584,835 show anchors adapted to be threaded into bores in bone and having apertures for receiving sutures. However, these structures are intended for use where the graft ligament is intended to lie substantially along the surface of a bone; the present invention is concerned with devices to be used at the end of bone tunnels and securing a suture extending inwardly through the bone tunnel.

Other patents show anchors for ligaments and similar structures wherein the structure to be fixed is sutured to an anchor threaded into a bone tunnel; see, for example, U.S. Pat. No. 5,156,616 to Meadows et al and U.S. Pat. No. 5,152,790 to Rosenberg et al. The art also suggests retaining a graft ligament in a bone tunnel by confining the ligament between a conical plug and the bone tunnel, so that the ligament is held in place by friction. See U.S. Pat. No. 4,744,793 to Parr et al and U.S. Pat. No. 4,708,132 to Silvestrini. It would be preferred to avoid the complexity of these types of anchor where possible.

Martins et al U.S. Pat. No. 5,306,290 shows a "Suture Button" comprising a frusto-conical member defining a recess for receiving a knot. This device could be placed in a bone tunnel and sutures from a graft ligament drawn through apertures in a planar surface forming the bottom of the recess; after suitably tensioning the ligament by tension applied to the suture, the knot can be tied, securing the ligament. However, this device would appear to be susceptible to being drawn into the bone tunnel by excessive tension.

Additional references show anchors for ligaments wherein the ligament is sutured to an anchor configured to abut the outer opening of the bone tunnel, and remain outside the bone tunnel. See for example Graf et al U.S. Pat. No. 5,306,301, disclosing various "elongated bodies" intended to be passed through the bone tunnels and rotated after exiting the tunnels, so as to be retained against the outer surface of the bone. See also U.S. Pat. No. 5,139,520 to Rosenberg, especially at column 11, lines 39–62.

German pat. no. DE 196 16 122 C1 to Eichborn et al is of the same general class and discloses several embodiments of anchor or "button" structures for securing ligaments in place. In one embodiment, the Eichborn anchor is of generally hat-shape configuration, comprising a round flange surrounding the rim of a hemispheric dome-shaped body having a depressed center section, forming a recess. The center section is sized to be received in the opening of a bone tunnel, and has apertures extending therethrough for receiving sutures, while the outermost flange portion of the Eichborn anchor abuts the outer surface of the bone, preventing the anchor from being pulled into the bone tunnel. The Eichborn anchor may be elliptical in outline, to conform to tunnels formed at an angle to the surface of the bone; see FIGS. 3 and 4. Accordingly, sutures can be passed through the apertures and tensioned and tied as discussed in connection with the Martins patent, to secure a graft ligament; the depressed recess receives the suture knot. The Eichborn anchor is of uniform thickness across the flange and dome, limiting its strength, and the placement of the suture-receiving apertures is not optimal for use in ligament reconstruction.

Other U.S. patents generally relevant to the subject matter of this application include U.S. Pat.No. 4,708,132 to Silvestrini; U.S. Pat. No. 4,744,793 to Parr et al; U.S. Pat. No. 5,571,139 to Jenkins, Jr.; U.S. Pat. No. 4,997,433 to Goble et al; U.S. Pat. No. 5,562,671, also to Goble et al; U.S. Pat. No. 5,261,914 to Warren; and U.S. Pat. No. 5,380,334 to Torrie et al.

OBJECTS OF THE INVENTION

It is therefore an object of the invention to provide an improved anchor for fixation of sutures with respect to bone, and correspondingly improved methods of doing so.

It is a more specific object of the invention to provide an anchor optimized for fixation of sutures used to tension a graft ligament with respect to a bone tunnel, and improved methods for securing a graft ligament in position within a bone tunnel.

SUMMARY OF THE INVENTION

The above objects of the invention and others appearing below are achieved by the anchor of the invention, and its use in securing sutures and thereby ligaments or other structures to bone. The anchor of the invention is of generally disc-shape configuration, having a round or elliptical flange surrounding the rim of a hemispheric dome-shaped body, having a depressed center section, forming a recess; the center section is sized to be received in the opening of a bone tunnel, and has apertures extending therethrough for receiving sutures, generally as in the case of the Eichborn anchor discussed above. However, unlike the Eichborn anchor, the anchor of the present invention is not of uniform thickness throughout, but is provided with additional thickness in areas of increased stress, particularly in the region of the apertures. In embodiments where the flange and possibly also the dome are of elliptical outline, the suture-receiving apertures are oriented so that tension applied to the sutures tends to maintain the anchor in a preferred orientation to the surface of the bone. This in turn allows the anchor to be formed of resorbable plastic material while providing sufficient pullout strength to allow significant tension to be exerted on the anchor by the sutures.

BRIEF DESCRIPTION OF THE DRAWINGS

The invention will be better understood if reference is made to the accompanying drawings, in which:

FIG. 1 shows the overall arrangement of a graft ligament in aligned bone tunnels drilled in the tibia and femur of a patient, and illustrates the employment of two differing embodiments of the anchor of the invention to secure the opposed ends of the graft ligament with respect to the bone tunnels in the tibia and femur;

FIG. 2 shows a plan view of a first embodiment of the anchor of the invention, and showing the disposition of sutures with respect to the anchor;

FIG. 3 shows an elevational view, partly in section, of the anchor of FIG. 2;

FIG. 4 shows a cross-sectional view taken along the line 4—4 in FIG. 2;

FIG. 5 shows an enlarged cross-sectional view corresponding to FIG. 4, without the sutures; and FIG. 6 shows a view corresponding to FIG. 5 of a second embodiment of the anchor of the invention, and illustrates a further possible modification.

DESCRIPTION OF THE PREFERRED EMBODIMENTS

FIG. 1 shows a cross-sectional view through the tibia 10 and femur 12 of a patient having had bone tunnels 10a and 12a respectively drilled therethrough from an entry wound in the skin over the tibia in accordance with the usual practice of the prior art. See the "Paramax ACL Guide System Surgical Technique" brochure referred to above. A graft ligament 15 is disposed extending between the two bone tunnels; in the embodiment shown, the graft ligament 15 is illustrated as having been taken from the patient's knee, and comprises a central section 16 of tendon and first and second bone portions 18 and 20 harvested from the patient's patella and tibia. As mentioned above, graft ligaments of other types are also within the scope of the invention.

According to the invention, one or two anchors 40, 42 fixed to the bone portions 18, 20 by sutures 44 are used to secure the graft ligament 15 in place, giving the bone portions 18 and 20 time to heal and be securely bonded to the femur and tibia respectively. After the graft ligament is disposed in its proper position, the sutures are tied off as shown, securing the graft ligament 15 in place. The anchors 40, 42 may be made of bioresorbable material, if intended simply to hold the ends of the graft 15 in place during the healing period, or may be of a permanent material if needed to provide strength indefinitely.

It will be appreciated by those of skill in the art that typically graft ligaments are fixed to the femur 12 by an anchor structure that can be placed through the tibial tunnel 10a or through a small incision in the femur, so as to minimize trauma to the overlying muscles and other structures; the anchor according to the invention may require a somewhat larger incision. (As the tibia is disposed just beneath the skin, such larger incisions cause less trauma when used to place anchors used to secure the tibial end of the graft.) Commonly, therefore, the anchor of the invention will be used only to secure the tibial end of the graft. However, two anchors according to the invention may indeed be used as shown, and are thus illustrated to conveniently describe various embodiments of the invention.

As shown in FIGS. 2, 3, and 4, the anchors of the invention comprise hemispherical domes 52 extending into the bone tunnels, locating the anchors positively with respect to the bone tunnels, and providing internal recesses for the knots of the sutures 44; this avoids irritation to the overlying tissues, and minimizes the discomfort caused to the patient. The anchor 42 comprises an outer flange 50 that may be circular or elliptical in outline, and a dome 52, which may be hemispherical, that is, rotationally symmetric, as illustrated in FIGS. 2–5, or may be asymmetric, as in the embodiment of FIG. 6. The asymmmetric anchor is also illustrated at 40 in FIG. 1, being used to secure the tibial end of the graft ligament. Alternatively, of course, the symmetrical anchor could be used at the tibial end.

As shown, two apertures 54 are formed in the dome portion 52 of the anchor, allowing passage of the sutures 44 by which the anchor is fixed to the graft ligament. In most cases, graft ligaments are to be secured to bone at an angle with respect to the outer surface of the bone well away from the perpendicular, as in the the case of ACL replacement illustrated in FIG. 1. Therefore, the stress exerted on the anchor by the sutures (noting that the anchors are intended to resist at least 100 pounds' tension) in most cases is taken along a line well off the perpendicular.

According to an important aspect of the invention, the anchor is asymmetrical in order to optimally resist the asymmetrical stress to which it is commonly subjected in use. For example, the flange is preferably elliptical, as shown in the plan view of FIG. 2, and in use is aligned such that the long axis (along line 4—4) is aligned with the tension exerted by the graft ligament. More specifically, the long axis of the elliptical flange is in the same plane as the stress; this plane corresponds to that on which FIG. 4 is taken. Correct alignment of the asymmetrical elliptical flange with the stress allows the flange to be optimally shaped. Stated differently, the elliptical flange provides sufficient surface area bearing on the outer surface of the bone to resist the tension exerted by the ligament. Providing equal resistance to tension with an anchor having a round flange would involve a significant increase in mass and size.

According to a further important aspect of the invention, the suture-receiving apertures 54, which may be of oval or racetrack configuration, as shown, are aligned on opposite sides of the long axis of the asymmetrical anchor, as shown in FIG. 2. In use, the sutures are spaced slightly from one another on either side of the plane including the long axis of the anchor and the stress; accordingly, the sutures exert tension equally on opposite sides of the anchor so that the anchor does not tend to twist or become dislodged during normal use.

By comparison, the Eichborn et al German patent also shows an anchor of asymmetric configuration, having an elliptical flange. However, it will be observed that the suture-receiving apertures are aligned along the long axis of the elliptical anchor. See FIG. 3. It will be appreciated by those of skill in the art that this is an unstable arrangement, which would tend to cause the anchor to twist when tension is exerted on the sutures.

According to a further aspect of the present invention, as shown in FIGS. 3 and 4, the cross-sectional dimension of the hemispherical portion of the anchor is relatively thick at the "saddle" 58 formed between the apertures 54, that is, at the point where the anchor resists the tension exerted by the sutures 44. This of course adds additional strength to the anchor in use and minimizes the possibility of tearing out of the sutures when tension is applied. More specifically, it is desired that at least a hundred pounds' tension can be withstood by the anchors; the advantage of providing this significant "pull-out strength" is that the patient can exert some force on the ligament during the healing period substantially immediately after surgery and need not wait for the bone portions of the graft ligament to knit fully to the tibia and femur before exercise.

FIG. 5 shows an enlarged view of the anchor 42 of FIGS. 2–4. As can be seen, the underside of the hemispherical dome portion 52 includes a relatively flat central surface 60 in the "saddle" region 58 between the apertures 54, increasing the thickness of the dome in this area, and further strengthening the anchor in an area where it would otherwise be weakened by the apertures 54 formed therethrough.

FIG. 6 shows a further embodiment of the invention wherein the anchor 40 comprises an asymmetrical dome portion 52' as well as an elliptical flange; stated differently, the anchor 40 of FIG. 6 is asymmetrical in the plane of FIG. 6, and will typically also include an elliptical flange 50, as shown in FIG. 2. More particularly, the anchor 40 of FIG. 6 (also shown in FIG. 1) is further optimized for use when the bone tunnel does not meet the outer surface of the bone at or near right angles, such that the direction of tension exerted by the sutures on the anchor is not perpendicular to the surface of the bone. As noted above, this circumstance is very common, particularly in ACL replacement. The FIG. 6 anchor 40 is formed in the asymmetrical manner shown so as to best resist the tension exerted by the sutures thereon. Specifically, both the dome portion 52' of the anchor 40 and the suture-receiving apertures 62 are not centered with respect to the dome as in the FIG. 5 embodiment, but are offset to one side, corresponding generally to the alignment of the bone tunnel 10*a* with respect to the outer surface of the bone. Normally, the flange will again be elliptical in plan and the apertures disposed opposite to one another, on either side of the long axis of the elliptical flange; the apertures are disposed on one side of asymmetric dome portion, between the apex of the dome and the flange, so as to be substantially aligned with the direction of extension of the sutures in use. Again, the dome portion 52' of the anchor has a flat under surface 60' so that the maximum thickness of the anchor is provided in the saddle area 58 between and around the apertures 62, again for strengthening.

In a further embodiment of the invention, the hemispherical portion could be further extended as indicated in dotted lines at 66 so that the dome portion 52' of the anchor 40 would contact and be braced against the inner wall of the bone tunnel 10*a*, substantially reducing possible deformation of the dome portion of the anchor due to tension exerted thereon by the sutures.

The method of replacing an ACL according to the invention therefore includes the steps of forming opposed bone tunnels in the tibia and femur; preparing a suitable graft ligament, either by harvesting from the patient's knee, or preparing an autograft or allograft ligament, all as shown in the prior art, and placing it in the bone tunnels, preferably with the sutures inserted; providing one or more of the anchors according to the invention; placing the anchor(s) such that when the paired cords of the sutures pass through apertures in the anchor the two apertures are on opposite sides of the line along which tension is exerted by the sutures, so that the anchor is unlikely to twist or become dislodged due to the tension exerted thereon; and suturing the graft to the anchors. Where, as is preferred, the flange of the anchor is elliptical in outline as shown in FIG. 2, the apertures are oriented transverse to the long axis of the elliptical anchor. Similarly, if the dome portion of the anchor is made asymmetrical by distorting the hemispherical shape in the direction of the stress, as in FIG. 6, the apertures 54 are opposed to one another, on either side of a line in the direction of the stress.

While a preferred embodiment of the invention has been described, further improvements thereto will be apparent to those of skill in the art. In particular, while the anchor of the invention is preferably a unitary member molded of a bio-resorbable material such as polylactic acid, such that the anchor will dissolve after the graft ligament has become bonded to the bone tunnels, non-bioresorbable materials can be used to permanently add strength to the ligament fixations. Other shapes of the dome and flange can be provided for particular embodiments. Accordingly, the invention should not be limited by the above exemplary disclosure, but only by the following claims.

What is claimed is:

1. An improved anchor for securing a replacement ligament in a bone tunnel drilled in a patient's bone, said anchor being a unitary member formed of a bioresorbable material, and comprising a first dome portion, adapted to fit into the bone tunnel, and a second flange portion surrounding said dome portion and adapted to rest on the surface of said bone surrounding said bone tunnel and prevent said anchor from being pulled into said bone tunnel, said dome portion having at least two apertures formed therein for passage of sutures therethrough, the cross-sectional thickness of the material of said dome portion of said anchor being greater in the vicinity of said apertures than elsewhere, and wherein said flange is elliptical in plan and said apertures are opposed to one another, on either side of the long axis of said elliptical flange.

2. The anchor of claim 1, wherein said dome portion has a flat inner surface at its apex.

3. The anchor of claim 1, wherein said dome portion is asymmetric, and said apertures are disposed on a side of said dome portion so as to be substantially aligned with the direction of extension of said sutures.

4. The anchor of claim 3, wherein said dome portion is shaped to fit closely within and be at least partially supported by said bone tunnel.

5. A method of anchoring a graft ligament disposed within a a bone tunnel with respect to said bone tunnel, comprising the steps of:

forming an aperture through a portion of the ligament to be anchored, passing a suture through said aperture, providing an anchor, said anchor being a unitary member formed of a bioresorbable material, and comprising a first dome portion, adapted to fit into the bone tunnel, and a second flange portion surrounding said dome portion and adapted to rest on the surface of said bone surrounding said bone tunnel and prevent said anchor from being pulled into said bone tunnel, said dome portion including at least two apertures for passage of sutures therethrough, said anchor being further formed such that said flange is elliptical in plan and said apertures are opposed to one another on either side of the long axis of said elliptical flange, aligning said at least two apertures transverse to the direction of tension exerted thereon by said sutures in use, passing said suture through said at least two apertures in said anchor, and tying said suture to exert a desired degree of tension on said graft ligament.

6. The method of claim 5, comprising the step of forming said anchor such that said dome portion has a flat inner surface at its apex.

7. The method of claim 5, comprising the step of forming said anchor such that said dome portion is asymmetric, and such that said apertures are disposed on a side of said dome portion, and the further step of aligning said apertures in use substantially with the direction of extension of said sutures.

8. The method of claim 7, comprising the step of shaping said dome portion to fit closely within and be at least partially supported by said bone tunnel.

* * * * *